United States Patent
Hamill et al.

(10) Patent No.: US 9,579,070 B2
(45) Date of Patent: Feb. 28, 2017

(54) OPTIMAL RESPIRATORY GATING IN MEDICAL IMAGING

(75) Inventors: James J. Hamill, Knoxville, TN (US); Ludovic Le Meunier, Los Angeles, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1072 days.

(21) Appl. No.: 13/248,089

(22) Filed: Sep. 29, 2011

(65) Prior Publication Data

US 2013/0085375 A1 Apr. 4, 2013
US 2014/0051977 A9 Feb. 20, 2014

Related U.S. Application Data

(63) Continuation-in-part of application No. 11/714,405, filed on Mar. 6, 2007, now Pat. No. 8,060,177.

(60) Provisional application No. 60/779,628, filed on Mar. 6, 2006.

(51) Int. Cl.
| | |
|---|---|
| A61B 5/00 | (2006.01) |
| A61B 6/00 | (2006.01) |
| A61B 5/113 | (2006.01) |
| A61B 6/03 | (2006.01) |
| G01R 33/48 | (2006.01) |
| G01R 33/567 | (2006.01) |

(52) U.S. Cl.
CPC .......... *A61B 5/7292* (2013.01); *A61B 5/1135* (2013.01); *A61B 6/037* (2013.01); *A61B 6/541* (2013.01); *G01R 33/481* (2013.01); *G01R 33/5676* (2013.01)

(58) Field of Classification Search
CPC ..... A61B 5/1135; A61B 5/7292; A61B 6/037; A61B 6/541; G01R 33/481; G01R 33/5676
See application file for complete search history.

(56) References Cited

U.S. PATENT DOCUMENTS

| | | |
|---|---|---|
| 2005/0201510 A1* | 9/2005 | Mostafavi ................ 378/8 |
| 2006/0178575 A1 | 8/2006 | Piacsek et al. |
| 2007/0232903 A1 | 10/2007 | Hamill |
| 2010/0067765 A1 | 3/2010 | Buther et al. |

(Continued)

OTHER PUBLICATIONS

GJ Klein et al., Fine-Scale Motion Detection Using Intrinsic List Mode PET Information, MMBIA 71-78 (2001).

(Continued)

*Primary Examiner* — Ruth S Smith

(57) ABSTRACT

Methods and computer-readable mediums are provided for obtaining an optimally gated medical image. For example, in one embodiment, a method is provided that acquires medical images in list mode. The method also acquires a respiration correlated signal S(t). Thereafter, a final upper strain threshold value and a final lower strain threshold value pair that has a narrowest interval are selected. The medical images are synchronized with the respiration correlated signal S(t). The synchronized images and signal are used to create an optimally gated medical image. In various embodiments, the disclosed optimal gating can be utilized in PET systems and in other embodiments the disclosed optimal gating can be utilized in SPECT systems. In yet other embodiments, the optimally gated images can be matched to MRI systems and in still other embodiments, the optimally gated images can be matched to CT systems.

16 Claims, 5 Drawing Sheets

(56) References Cited

U.S. PATENT DOCUMENTS

2010/0189324 A1     7/2010    Wollenweber et al.
2010/0290683 A1    11/2010    Demeester et al.

OTHER PUBLICATIONS

Chi Liu et al., Quiescent Period Respiratory Gating for PET/CT, 47 Am. Assoc. Phys. Med. 5037-5043 (2010).
Wouter Van Elmpt et al., Optimal Gating Compared to 3D and 4D PET Reconstruction for Characterization of Lung Tumours, 38 Eur. J. Nucl. Med. Mol. Imaging, 843-855 (2011).

\* cited by examiner

OPTIMAL RESPIRATORY GATING IN MEDICAL IMAGING

BACKGROUND

Field of the Invention

Embodiments of the present invention generally relate to diagnostic imaging systems. More particularly, the present invention relates to a method for performing emission computed tomography ("ECT") scanning, including positron emission tomography (PET) scanning and single photon emission tomography (SPECT). Embodiments of the present invention also provide for improved methods of gating medical images.

Description of the Related Art

Computed tomography ("CT") scanning (i.e., using an external X-ray source) and positron emission tomography ("PET") scanning using an infused radiopharmaceutical as a source of gamma ray emissions) are well known methods for diagnostic medical imaging. CT scanning employs multiple X-ray images taken in multiple directions to generate a 3-dimensional image or multiple tomographic image "slices." PET scanning employs a gamma-emitting radiopharmaceutical ingested by a patient or injected into a patient. Multiple gamma ray images are taken in multiple directions to generate a 3-dimensional PET image or multiple slices.

PET scanning requires a relatively long duration data acquisition period lasting several minutes per patient bed position. Typically, a large number of PET data acquisitions are acquired at many different angles during this period. Consequently, patient movement is a problem in PET scanning Excessive motion of a patient can result in reduced image fidelity, including an incorrect impression of the pattern of tracer uptake, and quantitative errors in which the wrong estimate of tracer concentration is made. Thoracic cage movement caused by breathing is a significant problem in PET scanning.

By comparison, CT scanning is relatively fast and can typically be performed during one breath-hold by a patient.

Part of the solution to the problem of respiration related image degradation is to provide gating of PET scanning based on measurement of certain triggering parameters associated with respiratory motion. In particular, it is known in the art to use a strain gauge to measure the tension in a strap placed around the abdomen or chest of a patient. The time-varying strain measurement is interpreted as a measure of respiratory amplitude and as such is used to develop information that can be used to gate or trigger the operation of imaging apparatus.

In the state of the art, the respiratory amplitudes are used to generate trigger signals, or gates, which indicate that a particular phase in the respiratory cycle has been reached. Commonly, triggers are generated at the end of each full breath, or end-inspiration, and the phase angle is assumed to vary smoothly from trigger to trigger. However, the phase-based approach has a limited ability to identify the actual state of breathing, since patient breathing patterns change over the time period involved in performing the diagnostic scan. This problem is illustrated in the strain gauge traces of FIG. 1. The traces show that deep, irregular breathing at one point in time can be followed by a more regular, shallower breathing pattern ten minutes later. In FIG. 1, the horizontal axis represents time, with a one minute interval between the left and right sides of each plot. The vertical axis represents the strain measurement value. Smaller values correspond to a more relaxed chest or shallow breathing. Larger values correspond to a more expanded chest or deep breathing.

Accordingly, there is a need in the art for improved methods for gating of medical images. It would be particularly beneficial to provide methods of creating medical images that can correct for inaccuracies caused by respiration.

SUMMARY

An aspect of the present invention generally includes a method for positron emission tomography (PET) imaging that overcomes the problems in the prior art. Optimal gating criteria are calculated based on the strain gauge levels, and a PET image is made in accordance with the optimal gating criteria. An aspect of the present invention is also applicable to SPECT.

Methods are provided for obtaining an optimally gated medical image. The method acquires a respiration correlated amplitude measurement S(t) at the same time that medical image measurements are acquired. Thereafter, the method determines an optimal pair of upper amplitude threshold value and lower amplitude threshold value by selecting the pair that has the narrowest possible interval between the upper and lower values. The respiratory amplitude measurements are synchronized with the medical image measurements, and these are used to create an optimally gated medical image. In various embodiments, the disclosed optimal gating can be utilized in positron emission tomography ("PET") systems, and in other embodiments the disclosed optimal gating can be utilized in single photon emission computed tomography ("SPECT") systems.

Other embodiments use optical tracking devices, a pneumatic sensor, ultrasound, or magnetic resonance imaging systems ("MRI") to acquire patient respiration data.

Other embodiments of the invention are also provided that utilize computer-readable mediums which provide features similar to the above methods.

BRIEF DESCRIPTION OF THE DRAWINGS

So that the manner in which the above recited features of embodiments of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, wherever possible, to designate identical elements that are common to the figures.

DETAILED DESCRIPTION

Embodiments of the present invention provide a method for positron emission tomography ("PET") scanning with compensation for patient respiratory motion.

Other embodiments of the invention also provide for improved gating (referred to hereinafter as "optimal gating") of medical images. Optimal gating, as disclosed herein, can be applied to radionuclide imaging modalities (e.g., PET and SPECT). The present application incorporates by reference all of the material in U.S. patent application Ser. No. 11/714,405 filed on Mar. 6, 2007, now U.S. Pat. No. 8,060,177 issued Nov. 15, 2011.

Figure 1:
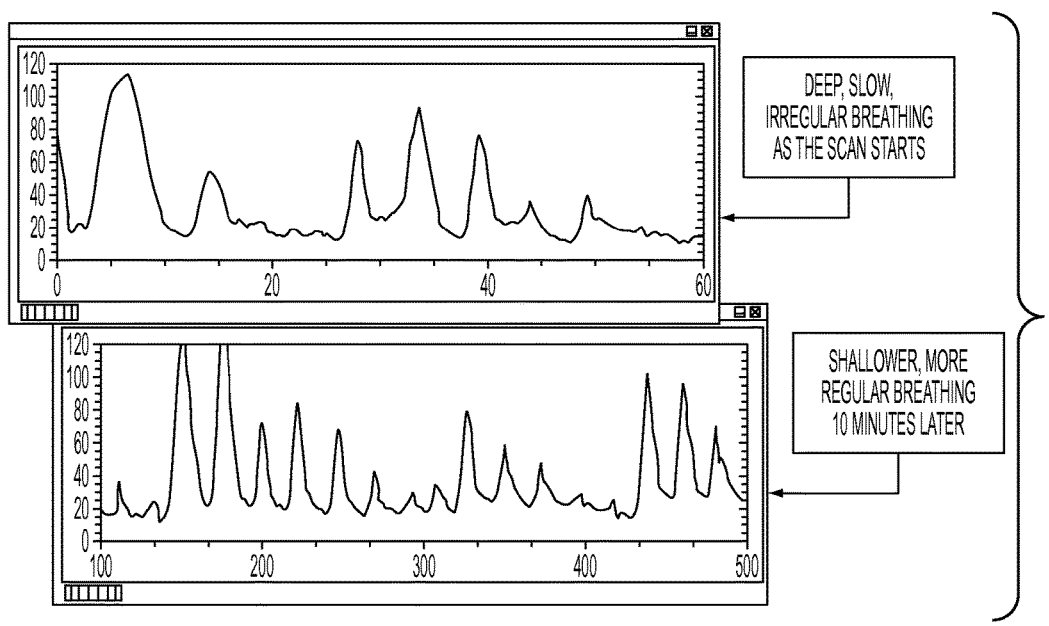
FIG. 1 shows strain gauge measurements of a patient's respiration over a period of time corresponding to an image scanning procedure in accordance with the prior art.
Figure 2:
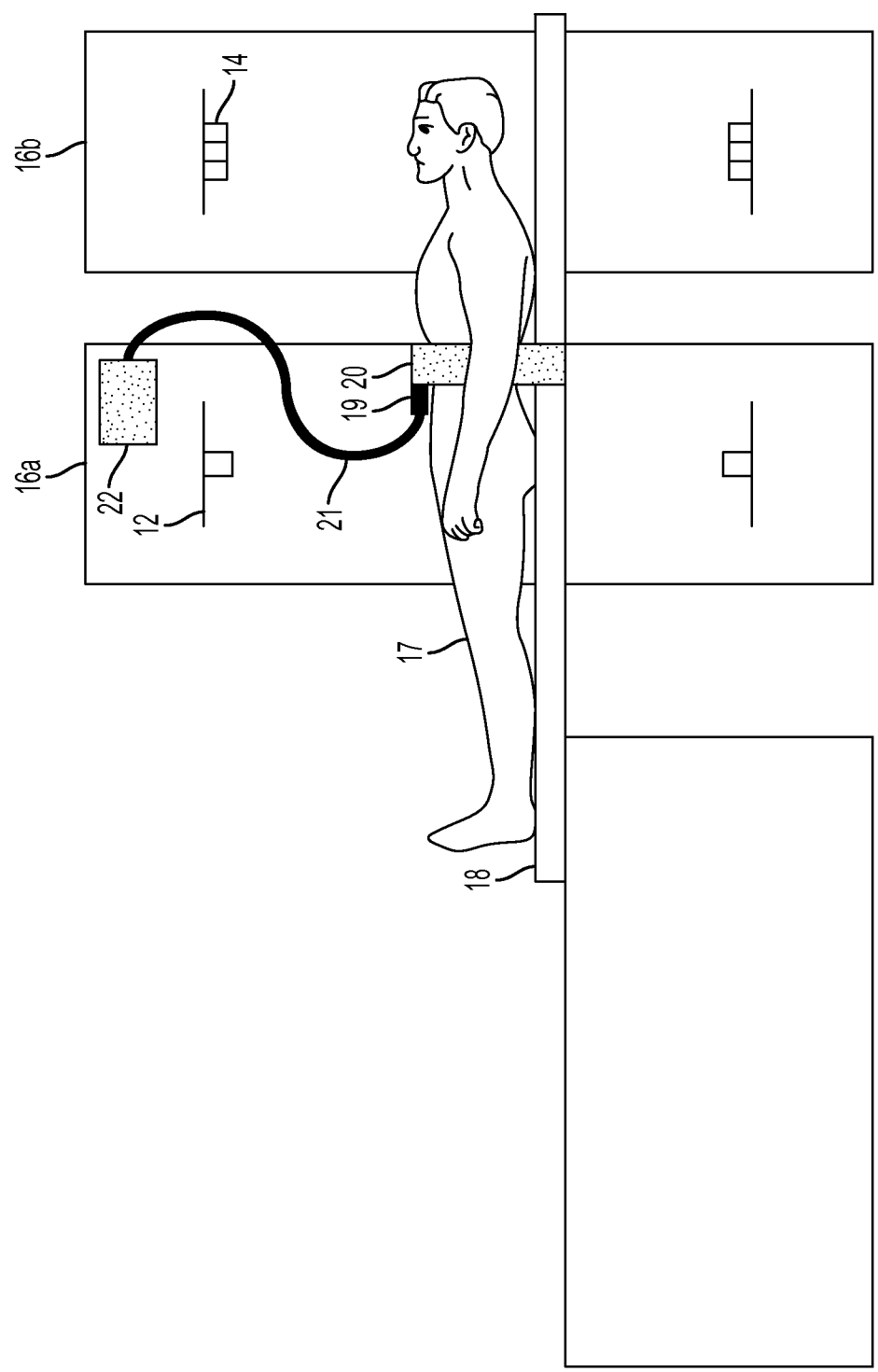
FIG. 2 shows an imaging device for sequentially performing CT and PET scanning, which can be used in accordance with embodiments of the present invention.

Embodiments of the invention can be performed using a PET scanner that can acquire image data in list mode. FIG. 2 shows one example of a combination PET/CT apparatus that can be used with the present invention. The CT scanner provides a three dimensional image of patient anatomy, which is used to estimate the attenuation of the annihilation radiation imaged by the PET scanner, a well-understood procedure. The apparatus includes a CT scanner 16a (having detectors 12) and a PET scanner 16b (having detectors 14) in a common gantry (although not shown, it is appreciated that in other embodiments of the invention, the CT scanner 16a and the PET scanner 16b can be in separate gantries). A patient 17 lies on a patient bed 18, that is movable between the CT 16a and PET 16b scanners. The patient's respiration is monitored by a strain gauge 19 which is held against the patient's thorax with a belt 20. Electrical signals from the strain gauge 19 are communicated through a cable 21 to a respiratory monitoring system 22.

Figure 5:
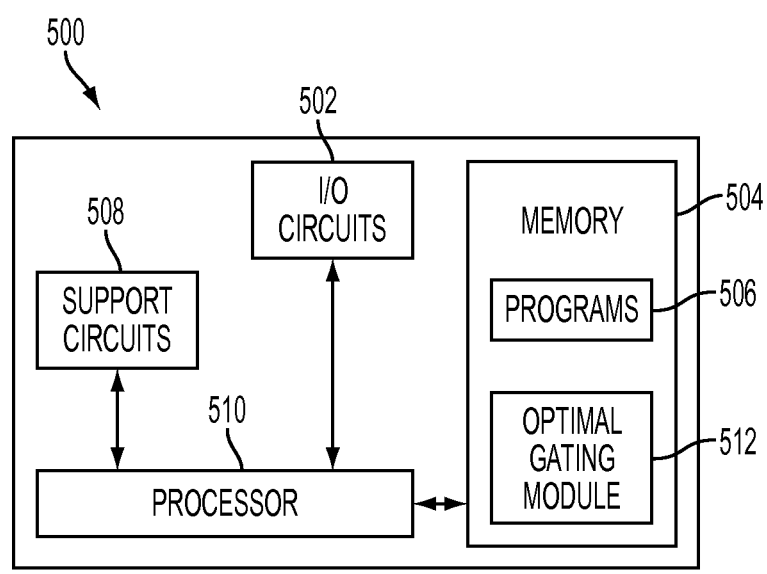
FIG. 5 depicts an embodiment of a high-level block diagram of a general-purpose computer architecture 500 for providing optimal gating in accordance with embodiments of the invention.

The respiratory monitoring system is also shown as processor 510 in FIG. 5. The processor periodically samples and digitizes the strain measurements and inserts the digitized measurement into the PET data stream. Synchronization of the respiratory amplitude measurements with the medical image measurements is essential. The latency associated with measurement insertion must be a small fraction of the respiratory cycle. This condition is realized routinely in modern PET and PET/CT systems, where the latency is a small fraction of one second.

Figure 3:
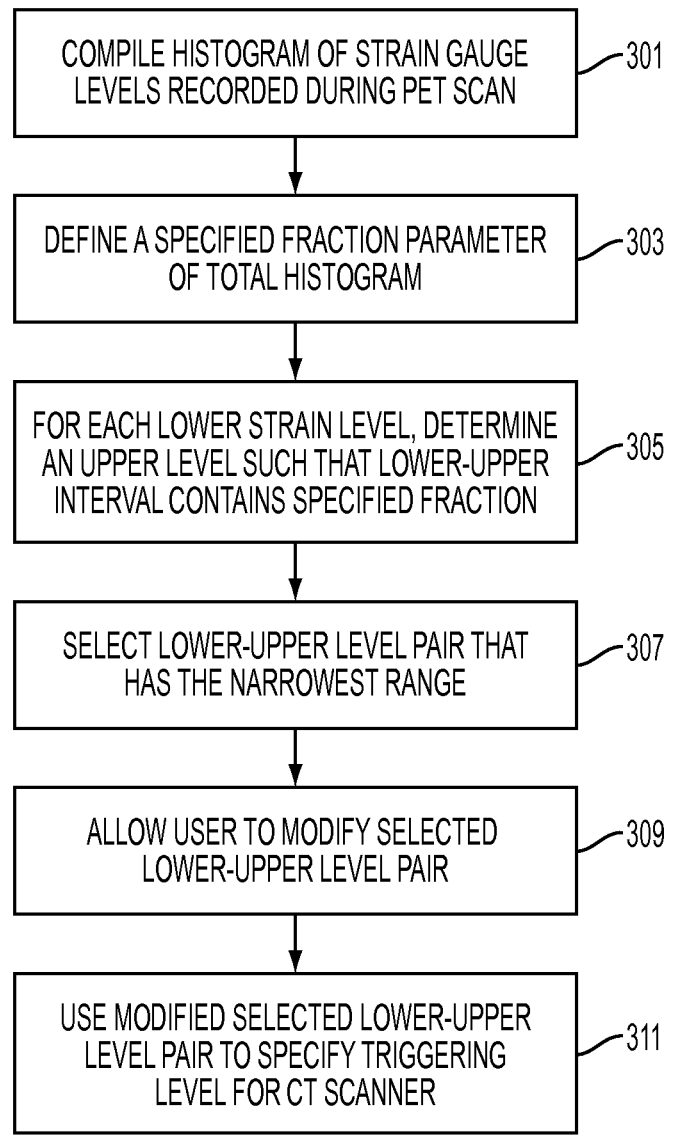
FIG. 3 is a flow diagram of a process for determining an upper and lower strain level pair to be used for developing a PET gating criterion.
Figure 4:
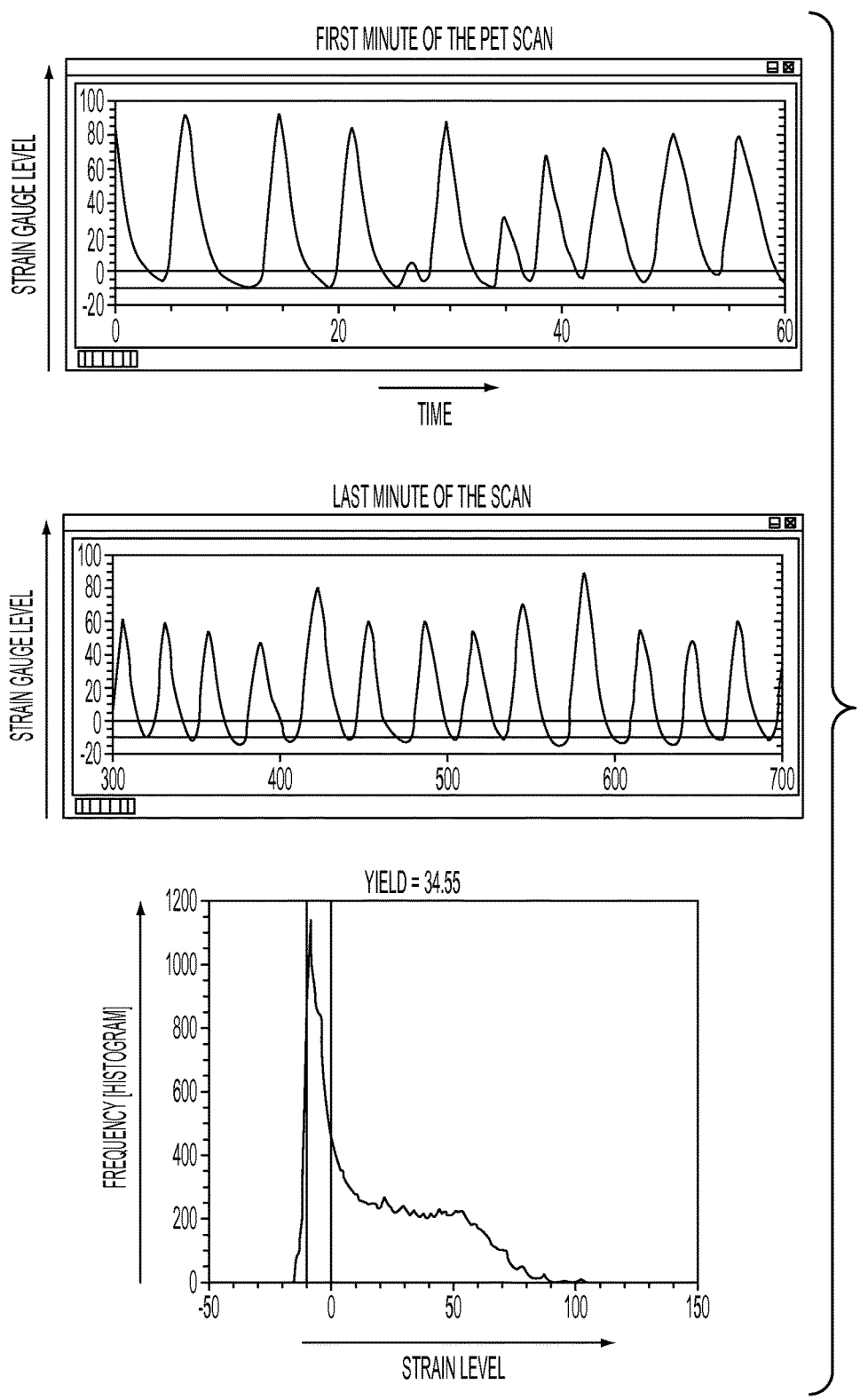
FIG. 4 shows a strain measurement constructed in accordance with the process of FIG. 3 (the top two panels) and the corresponding histogram of strain measurements.

After the PET list mode data and strain level measurement data are acquired, the procedure advances to a computational process as shown in FIG. 3. In step 301, a histogram of respiratory amplitude measurements is compiled, as shown in FIG. 4. At step 303, a specified fraction parameter is defined, which is some major fraction of the entire histogram. Next, at step 305 each lower respiratory amplitude level is considered, and a respiratory amplitude upper level is determined such that the interval defined by the lower and upper levels contains the predefined fraction of the entire histogram. This process is repeated for all lower strain levels.

At step 307, the lower and upper level pair is selected that has the narrowest range of level values, i.e., the lower-upper level combination that minimizes the difference between the two levels. This process leads to an automatic recommendation of a strain levels pair that encompasses a high fraction of the total PET acquisition time, while at the same time corresponding to a relatively small amount of chest excursion. For example, Equation (1) below represents an equation used in an algorithm that considers upper and lower strain levels. The algorithm considers all possible L values, and for each one it chooses a U(L) value which makes the sum between L and U(L) as close as possible to F. That is $$U(L) = \mathrm{argmin}\left\{\left|F - \sum_{S=L}^{U(L)} H(S)\right|\right\} \quad \text{Equation (1)}$$

where F represents the user selected percentage, H(S) represents a respiratory signal level (i.e., amplitude) in a histogram, L represents a lower strain level, and U(L) represents an upper strain level.

This is illustrated in the PET scan respiration traces shown in FIG. 4.

At step 309, the operator is allowed to modify the recommended strain levels pair, by adjusting if desired either the lower level, upper level, both lower and upper level, or no level adjustment.

At any point in time, the gate is either open or closed depending on the value of S(t). The gate is open if $L \leq S \leq U$, closed otherwise. Medical image measurements made when the gate is open (i.e., PET events that occur when $L \leq S \leq U$) are used to form the optimally gated medical image.

The optimally gated medical image can be one of three types. The first type of optimally gated image is a static respiratory gated image, which uses events acquired when the respiratory gate is open but no other requirements are imposed. This type of image is made with no need to issue breathing instructions to the patient. The second type of optimally gated image additionally is a cardiac and respiratory gated image. This type of image is based on cardiac trigger signals present in the data list. It is well known in the state of the art that cardiac gated images can be formed by dividing the interval from one trigger to the next into several cardiac gates. Data from a large number of heartbeats are combined into a single image. Although this state of the art provides the ability to select just one phase of cardiac motion, all states of respiratory motion are present, which causes image blurring. It is possible in principle to arrest the respiratory motions by imaging only during a breath hold, but patients cannot hold their breath long enough to make a good image by PET or SPECT. By combining cardiac and respiratory gating criteria, a good image can be made in which image blurring due to breathing motions is largely eliminated, and breathing instructions are not needed. The third type of optimally gated image is a dynamic respiratory gated image. In the state of the art, dynamic imaging is used to separately frame data acquired in different time periods of the acquisition, so that one can observe changes in tracer distribution from the beginning to the end of the scan. For example, in a ten-minute scan with two-minute time frames, the first frame is based on all events acquired in the first two-minute period of the scan, the second frame is based on all events acquired in the second two-minute period of the scan, and so on. However, in this state of the art, each dynamic frame is degraded by breathing motion. By combining time framing and respiratory gating criteria, a good image can be made in which image blurring due to breathing motions is largely eliminated.

FIG. 5 depicts an embodiment of a high-level block diagram of a general-purpose computer architecture 500 for providing optimal gating in accordance with embodiments of the invention. The general-purpose computer of FIG. 5 includes a processor 510 as well as a memory 504 for storing control programs and the like. In various embodiments, memory 504 also includes programs (e.g., depicted as an "optimal gating module" 512 for creating PET images) for performing the embodiments described herein. The processor 510 cooperates with conventional support circuitry 508 such as power supplies, clock circuits, cache memory and the like as well as circuits that assist in executing the software routines 506 stored in the memory 504. As such, it is contemplated that some of the process steps discussed herein as software processes can be loaded from a storage device (e.g., an optical drive, floppy drive, disk drive, etc.) and implemented within the memory 504 and operated by the processor 510. Thus, various steps and methods of the present invention can be stored on a computer readable medium. The general-purpose computer 500 also contains input-output circuitry 502 that forms an interface between the various functional elements communicating with the general-purpose computer 500.

Although FIG. 5 depicts a general-purpose computer 500 that is programmed to perform various control functions in accordance with the present invention, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. In addition, although one general-purpose computer 500 is depicted, that depiction is for brevity on. It is appreciated that each of the methods described herein can be utilized in separate computers.

In other embodiments of the invention, the respiratory amplitude is measured by an instrument other than a strain gauge. For example, devices commonly used in radiation therapy use digital cameras to optically track of the position of a marker placed on the patient's abdomen. Associated circuitry and computers in these devices supply a respiratory amplitude measurement which is communicated to the imaging system. Another example, commonly used in stand-alone magnetic resonance imaging scanner examinations (MRI), is a pneumatic device which generates an electronic signal corresponding to the air pressure in a flexible bladder held against the thorax and held tightly in place with a strap. Another example occurs in the case of a PET scanner operating in the field of view of an MRI scanner. In this case, routinely available MRI imaging sequences and image processing hardware software provide many images per second of anatomical landmarks that move with the patient's respiration. Computerized methods identify the positional coordinates of the anatomical landmark in each image and convert this information to a respiration-correlated amplitude measurement that varies with time as the patient breathes. A familiar version of this technology is the so-called MRI navigator, which follows the respiratory motions of the patient's diaphragm.

While the foregoing is directed to embodiments of the present invention, other and further embodiments of the invention may be devised without departing from the basic scope thereof, and the scope thereof is determined by the claims that follow.

We claim:

1. A method of forming an optimally gated medical image comprising:
   acquiring a list mode data set for medical imaging of a patient;
   simultaneously acquiring from said patient a respiration correlated amplitude measurement S(t), said respiration correlated amplitude measurement S(t) including respiration amplitude threshold value pairs;
   selecting a lower respiration amplitude threshold value and an upper respiration amplitude threshold value pair that has a narrowest interval from among all respiration amplitude threshold value pairs in said measurement S(t);
   synchronizing the list mode data set and the respiration correlated amplitude measurement; and
   using list mode data of said list mode data set obtained when said measurement S(t) was within a range defined by said lower and upper threshold values to form a medical image.

2. The method of claim 1 wherein synchronizing the list mode measurement and the respiration correlated amplitude measurement comprises synchronously injecting samples of said respiration correlated amplitude measurement into said list mode data set.

3. The method of claim 1 wherein acquiring said list mode data set for medical imaging comprises acquiring list mode data from one of a positron emission tomography (PET) device and a single photon emission computed tomography (SPECT) device.

4. The method of claim 1 wherein acquiring said list mode data set for medical imaging comprises acquiring list mode data from one of a positron emission tomography (PET) device and a single photon emission computed tomography (SPECT) device that is part of a system including one of a computed tomography (CT) system and a magnetic resonance imaging (MRI) system.

5. The method of claim 1 wherein said medical image comprises a cardiac gated image, a dynamic medical image, or a static medical image.

6. The method of claim 1 wherein acquiring said respiration correlated amplitude measurement S(t) comprises acquiring said measurement S(t) from one of a strain gauge, a pneumatic sensor, and a magnetic resonance imaging (MRI) scanner view of an anatomical landmark.

7. The method of claim 1 wherein said selection of said threshold value pair comprises:
   compiling a histogram of respiration correlated amplitude measurements;
   selecting a fraction parameter, wherein the fraction parameter comprises a predetermined portion of said histogram;
   selecting a lower respiration correlated amplitude measurement threshold value from measured lower respiration amplitude levels; and
   selecting upper respiration correlated amplitude measurement threshold values for each measured lower respiration correlated amplitude measurement level, wherein an interval defined by said upper respiration correlated amplitude measurement threshold values and said lower respiration amplitude threshold value includes said predetermined portion of said histogram.

8. The method of claim 1 wherein said selection of said threshold value pair comprises solving the equation $$U(L) = \mathrm{argmin}\left\{\left|F - \sum_{S=L}^{U(L)} H(S)\right|\right\}$$

where F represents a user selected percentage, H(S) represents a respiratory amplitude in a histogram, U(L) represents an upper respiration amplitude threshold level, and L represents a lower respiration amplitude threshold level.

9. A non-transitory computer-readable medium having stored thereon a plurality of processor-executable instructions, which when executed by a processor, cause the processor to:
- acquire a list mode data set for medical imaging of a patient;
- simultaneously acquire from said patient a respiration correlated amplitude measurement S(t), said respiration correlated amplitude measurement S(t) including respiration amplitude threshold value pairs;
- select a lower respiration amplitude threshold value and an upper respiration amplitude threshold value pair that has a narrowest interval from among all respiration amplitude threshold value pairs in said measurement S(t);
- synchronize the list mode data set and the respiration correlated amplitude measurement; and
- use list mode data of said list mode data set obtained when said measurement S(t) was within a range defined by said lower and upper respiration amplitude threshold values to form a medical image.

10. The computer-readable medium of claim 9 wherein said instruction causing synchronizing the list mode measurement and the respiration correlated amplitude measurement comprises an instruction causing the processor to synchronously inject samples of said respiration correlated amplitude measurement into said list mode data set.

11. The computer-readable medium of claim 9 wherein said instruction causing acquiring of a list mode data set for medical imaging comprises an instruction causing the processor to acquire list mode data from one of a positron emission tomography (PET) device and a single photon emission computed tomography (SPECT) device.

12. The computer-readable medium of claim 9 wherein said instruction causing acquiring of a list mode data set for medical imaging comprises an instruction causing the processor to acquire list mode data from one of a positron emission tomography (PET) device and a single photon emission computed tomography (SPECT) device that is part of a system including one of a computed tomography (CT) system and a magnetic resonance imaging (MRI) system.

13. The computer-readable medium of claim 9 wherein said medical image comprises a cardiac gated image, a dynamic medical image, or a static medical image.

14. The computer-readable medium of claim 9 wherein said instruction causing acquiring said respiration correlated amplitude measurement S(t) comprises an instruction causing the processor to acquire said measurement S(t) from one of a strain gauge, a pneumatic sensor, and a magnetic resonance imaging (MRI) scanner view of an anatomical landmark.

15. The computer-readable medium of claim 9 wherein said instruction causing selection of said threshold value pair comprises instructions causing the processor to:
- compile a histogram of respiration correlated amplitude measurements;
- select a fraction parameter, wherein the fraction parameter comprises a predetermined portion of said histogram;
- select a lower respiration correlated amplitude measurement threshold value from measured lower respiration amplitude threshold levels; and
- select upper respiration correlated amplitude measurement threshold values for each measured lower respiration correlated amplitude measurement level, wherein an interval defined by said upper respiration correlated amplitude measurement threshold values and said lower respiration amplitude threshold value includes said predetermined portion of said histogram.

16. The computer-readable medium of claim 9 wherein said instruction causing selection of said threshold value pair comprises an instruction for solving the equation $$U(L) = \mathrm{argmin}\left\{\left|F - \sum_{S=L}^{U(L)} H(S)\right|\right\}$$

where F represents a user selected percentage, H (S) represents a respiratory amplitude in a histogram, U(L) represents an upper respiration amplitude threshold level, and L represents a lower respiration amplitude threshold level.

* * * * *